United States Patent
Mirajkar et al.

(10) Patent No.: US 10,138,447 B2
(45) Date of Patent: Nov. 27, 2018

(54) FRAGRANCE INTENSITY ENHANCED PRODUCTS AND METHODS THEREFOR

(71) Applicant: COLGATE-PALMOLIVE COMPANY, New York, NY (US)

(72) Inventors: Yelloji-Rao K. Mirajkar, Piscataway, NJ (US); Amjad Farooq, Hillsborough, NJ (US); Amy Engels, Marlboro, NJ (US)

(73) Assignee: Colgate-Palmolive Company, New York, NY (US)

( * ) Notice: Subject to any disclaimer, the term of this patent is extended or adjusted under 35 U.S.C. 154(b) by 88 days.

(21) Appl. No.: 15/102,107

(22) PCT Filed: Nov. 21, 2013

(86) PCT No.: PCT/US2013/071179
§ 371 (c)(1),
(2) Date: Jun. 6, 2016

(87) PCT Pub. No.: WO2015/076805
PCT Pub. Date: May 28, 2015

(65) Prior Publication Data
US 2016/0355768 A1 Dec. 8, 2016

(51) Int. Cl.
| | | |
|---|---|---|
| C11D 17/04 | (2006.01) |
| A61L 9/012 | (2006.01) |
| B65D 51/24 | (2006.01) |
| B65B 5/04 | (2006.01) |
| B65B 63/08 | (2006.01) |
| B65D 1/02 | (2006.01) |
| C11D 3/50 | (2006.01) |
| B65D 85/10 | (2006.01) |

(52) U.S. Cl.
CPC .............. *C11D 17/04* (2013.01); *A61L 9/012* (2013.01); *B65B 5/04* (2013.01); *B65B 63/08* (2013.01); *B65D 1/02* (2013.01); *B65D 51/24* (2013.01); *C11D 3/50* (2013.01); *B65D 85/1045* (2013.01); *B65D 2203/12* (2013.01)

(58) Field of Classification Search
CPC ........... C11D 17/04; C11D 3/50; A61L 9/012; B65D 1/02; B65D 51/24; B65D 2203/12; B65D 85/1045; B65B 5/04; B65B 63/08
USPC ................. 516/98; 512/4; 206/264; 220/294
See application file for complete search history.

(56) References Cited

U.S. PATENT DOCUMENTS

| | | | | |
|---|---|---|---|---|
| 5,165,603 A | * | 11/1992 | Hahn ................. | A45D 40/0068 206/823 |
| 5,175,142 A | * | 12/1992 | Dervieux ................ | A61F 6/005 206/221 |
| 5,297,732 A | | 3/1994 | Hahn | |
| 5,637,401 A | * | 6/1997 | Berman ............. | A45D 40/0087 424/59 |
| 5,679,334 A | * | 10/1997 | Semoff ..................... | A61L 9/01 424/76.3 |
| 5,780,527 A | * | 7/1998 | O'Leary ................. | A61L 9/042 512/4 |
| 6,045,835 A | * | 4/2000 | Soper ....................... | B01J 13/10 264/4.3 |
| 6,214,063 B1 | * | 4/2001 | DeStefano ................ | C10L 5/40 44/275 |
| 6,242,509 B1 | * | 6/2001 | Berger .................... | A61K 8/042 424/400 |
| 6,511,726 B1 | | 1/2003 | Kinigakis | |
| 7,754,198 B2 | | 7/2010 | Whitehead et al. | |
| 8,272,562 B2 | * | 9/2012 | Ziegler ................. | G09F 3/0335 235/375 |
| 2001/0019021 A1 | * | 9/2001 | Riviello, Jr. ........... | B65D 51/24 206/0.5 |
| 2003/0024997 A1 | | 2/2003 | Welch et al. | |
| 2005/0048279 A1 | | 3/2005 | Watson et al. | |
| 2005/0272878 A1 | | 12/2005 | Corzani et al. | |
| 2006/0246265 A1 | * | 11/2006 | Rogers ................... | B41M 3/006 428/195.1 |
| 2006/0249592 A1 | | 11/2006 | Burrowes et al. | |
| 2007/0108759 A1 | | 5/2007 | D'Amico | |
| 2007/0207174 A1 | * | 9/2007 | Pluyter .................... | A61K 8/11 424/401 |
| 2009/0053388 A1 | | 2/2009 | Crump | |
| 2011/0253584 A1 | * | 10/2011 | Duan ........................ | B32B 9/02 206/524.6 |
| 2012/0085828 A1 | | 4/2012 | Ziegler | |
| 2013/0043245 A1 | * | 2/2013 | Griffis .................. | B65D 51/245 220/200 |
| 2017/0239382 A1 | * | 8/2017 | Griffis ........................ | A61L 9/12 |
| 2018/0201877 A1 | * | 7/2018 | Maldonado Ortega .. | C11D 1/37 |

FOREIGN PATENT DOCUMENTS

| | | |
|---|---|---|
| EP | 2 548 816 | 1/2013 |
| GB | 2 385 525 | 8/2003 |

OTHER PUBLICATIONS

International Search Report and the Written Opinion of the International Searching Authority issued in International Patent Application PCT/US2013/071179 dated Mar. 18, 2014.

* cited by examiner

*Primary Examiner* — Daniel S Metzmaier

(57) ABSTRACT

Disclosed are products incorporating fragrance-enhancing compositions, methods for increasing the fragrance intensity of fragrance-containing products, and methods for the manufacture of the fragrance-containing products. A fragrance containing gel is exposed to a space outside of the container upon opening of the container for dispensing a material from the container.

16 Claims, No Drawings

FRAGRANCE INTENSITY ENHANCED PRODUCTS AND METHODS THEREFOR

BACKGROUND

Fragrances are used in a wide variety of products, including for example soaps, personal care and laundry products. Fabric softeners and conditioner formulations contain fragrance, usually as a fragrance oil, to impart a feeling of cleanliness and freshness to the fabric, and also to provide a pleasant experience to consumers. Sampling of such fragrances at the point of purchase, and at the place of use enhances the experience of the consumer, and may influence the decision of which product to purchase. Thus, enhancing fragrance intensity would provide both aesthetic and economic benefit.

BRIEF SUMMARY

Provided is a product container comprising a fragrance-containing gel that is disposed on the container and is not exposed to a space outside of the container, and the fragrance-containing gel is exposed to the space outside of the container upon opening of the container for dispensing a material from the container.

In one embodiment, provided is a method of promoting the sale of a product to a consumer, comprising providing a product container comprising a fragrance-containing gel disposed on a surface thereof, wherein the fragrance can be sampled by the consumer prior to purchase. In some particular embodiments, the fragrance-containing gel is disposed on an interior surface of the product container; for example on an interior surface within the headspace of the product container, e.g., wherein the product container is as described below.

In another embodiment, provided is a product container comprising a lid, cap or cover, wherein a fragrance-containing gel is disposed on an interior surface of the lid, cap or cover. In some further embodiments, the product container is bottle, a jar, a carton, a box, a dispensing package. Preferably, the product container includes, or is composed of, one or more of paper, cardboard, plastic or glass. In some embodiments, the lid, cap or cover of the product container is composed of or includes paper, cardboard, plastic or glass, or a combination of one or more thereof. In some further embodiments, the lid or cap is a screw cap, snap-on cap, a press-on cap, a twist cap, a fold-out lid, a fold-out or pull-out dispenser or spout, (e.g., metal fold-out dispenser in dishwasher detergent boxes).

In some embodiments, the product container is:
a fabric softener or conditioner container;
a laundry detergent container (including whiteners and brighteners);
a dishwasher detergent container (for example a box, having for example a fold-out pour spout or other dispenser);
a light liquid dishwashing detergent container;
a healthcare product container;
an air freshener container (including household, industrial and automobile air freshener containers and packages);
a personal care product container, including a shower gel container, a hand soap container, or an antiperspirant or deodorant container;
a candle container;
a hard surface cleaner container, for example a window cleaner container, a counter or floor cleaner container, or a disposable wipe container.

In some particular embodiments, the product container is a fabric softener or conditioner container, preferably having a screw cap or lid or a snap-on cap or lid.

In some embodiments, the fragrance-containing gel contains from 30% to 95% fragrance by weight of the fragrance-containing gel; or from 45% to 95%; or from 45% to 75%; or from 75% to 95%; or from 85% to 95% fragrance by weight of the fragrance-containing gel.

Also provided are methods for enhancing the fragrance intensity of a product in a package, the method comprising the step of disposing a fragrance-containing gel on a surface, for example an interior surface, of the package, preferably on an interior surface of the product lid, cap or cover.

Also provided is a use of a fragrance containing gel disposed on a surface, for example an interior surface of a product container, preferably on an interior surface of the product lid, cap or cover, for increasing fragrance perception of a product contained in the product container or for promoting the sale of a product to a consumer.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

It has been discovered that placement of fragrance-containing gel on a surface, for example an interior surface, of a product container or package, preferably on an interior surface within the headspace of the product container, enhances the fragrance intensity of the product. Thus, in some embodiments, provided are product containers comprising a fragrance-containing gel disposed on a surface thereof. In some particular embodiments, the fragrance-containing gel disposed on an interior surface of the product container, for example on an interior surface within the headspace of the product container.

As used herein, the term "interior surface" is intended to include any surface of the product container or package that is on the inside of the product container or package, including for example the inside surfaces of bottles, jars, cartons, boxes, dispensing packages, and their caps, lids, covers, pour spouts, and other integrated dispensing mechanisms.

As used herein, the term "product container" is intended to mean any of the wide variety of containers and packages in which consumer products are sold. Thus, product containers include bottles, jars, cartons, boxes, and other consumer product packages, including tear-open packages (for example plastic packages).

As used herein, the term "headspace" as used in conjunction with a product container is intended to refer to the space occupied by air or other gas inside a product container that contains a liquid, solid or gel product. The headspace is typically, but not necessarily, located above the product in the package, for example in the area above the liquid in a bottle containing a liquid product.

As used herein, "dispensed" means that a product in the container is removed from the container by pouring (as is in the case of fluids or flowable solids such as powders) or by physical contact of the material to a surface as is the case for a solid material, such as an antiperspirant stick). In certain embodiments, dispensed does not include materials that are not poured or contacted with a surface, such as an air freshener that is exposed to air.

In some embodiments, a product container can comprise a lid, cap or cover, and the fragrance-containing gel can be disposed, for example, on an interior surface of the lid, cap or cover. Typically, the fragrance containing gel is applied to the interior surface, e.g., the interior surface of a lid, cap or cover, at an elevated temperature, for example by heating a gelling composition containing fragrance to a temperature at which it has suitable mixing and flow properties, such that it forms a uniform solution or suspension and can be more easily applied to the product container surface. In some embodiments, the gelling composition is a fragrance containing gel. Such fragrance containing gets are known in the art and are commercially available. Typically, the gelling composition is heated to, for example and not limitation, temperatures greater than or equal to 35° C., 40° C., 50° C., 55° C., 60° C., 65° C. or 70° C. The composition is applied to the product container surface by any convenient technique, including for example and not limitation those techniques used to dispose glue, ink or other compositions on product packaging, for example and not limitation by brush, spray or roller, or by pouring a melted fragrance-containing composition into the cap or lid, and allowing the gelling composition to cool. Upon cooling, the gelling composition forms a gel, which releases fragrance over time, thus enhancing the amount of fragrance in the head space of the product container.

A variety of fragrance-containing gels can be employed in the methods and products. For example, fragrance-containing gels include those described in U.S. Pat. No. 7,754,198. Typically, the fragrance-containing gel contains an amount of fragrance (per volume or weight) that is grater than the amount of fragrance (per volume or weight) present in the product itself. For example, the fragrance-containing gels typically contain from 30% to 95% fragrance by weight of the fragrance-containing gel; or from 45% to 95%; or from 45% to 75%; or from 75% to 95%; or from 85% to 95% fragrance by weight of the fragrance-containing gel. In contrast, the fragrance-containing products typically contain less than or equal to 5%, 2% or 1% fragrance by weight.

The fragrance-containing gels can be disposed on any of a wide variety of product containers or packages known to be useful for packaging of fragrance-containing products, for example and not limitation bottles, jars, cartons, boxes, and dispensing packages such as those having plastic slit windows to dispense single sheets of product (for example tissues, sheet fabric softeners and other paper, cloth or cloth-like products containing fragrance). The product containers can be composed of, and/or include components (such as lids, covers, caps, etc.) composed of one or more of paper, cardboard, plastic, metal, wood or glass.

The product containers and packages can contain a lid, cap or cover, which can include any of the lids, caps and covers known to be useful for packaging of fragrance-containing products, including without limitation snap-on, twist-on, screw-on, press-on and partially perforated (i.e., such that separating a perforation creates a lid or cover) lids, caps or covers, as well as fold-out lids, and fold-out or pull-out dispensers or spouts, for example such as the paper, plastic or metal pours pouts typically used in paperboard cartoning (e.g., such as those sold by Seal-Spout Corporation). In one particular embodiment, the product container is a fabric softener or conditioner container, having a snap-on or screw-on cap or lid.

The containers, packages and methods can be used in conjunction with any product for which an added or enhanced fragrance is desired, including both fragrance-containing products and products that lack fragrance. As used herein, the term "fragrance-containing product" includes any product that contains a fragrance, whether or not the delivery of a fragrance is a primary purpose of the product. For example, scented tissues, scented stationary and dishwashing detergent are examples of fragrance-containing products, although delivery of fragrance is not the primary function of the product.

Thus, product containers can include, for example and not limitation:
a fabric softener or conditioner container;
a laundry detergent container including whiteners and brighteners);
a dishwasher detergent container;
an air freshener container (including household, industrial and automobile air freshener containers);
a healthcare product container;
a personal care product container, including a shower gel container, a handsoap container, an antiperspirant or, deodorant container, or a shampoo or conditioner container;
a candle container;
a household cleaner container, including a window cleaner container, a hard surface cleaner container, a disposable wipe container, or a dishwasher detergent or rinse aid container.

In one particular embodiment, the product container is a fabric softener or conditioner container, having a screw-on or snap-on cap, lid or cover.

As discussed above, in some embodiments, the product containers contain pour spouts to dispense the product, for example a box or carton, having for example a fold-out lid, or fold-out dispenser such as a pour spout. In some such embodiments, the fragrance containing gel can be disposed, for example, on the pour spout, or on an internal surface near the pour spout, to achieve a greater degree of fragrance enhancement to the end user.

Also provided are methods for enhancing the fragrance intensity of a product in a package or container, the method comprising the step of disposing a fragrance-containing get on an interior surface of the package or container, preferably on an interior surface of the product lid, cap or cover.

In some embodiments, the methods include the steps of:
i) providing a fragrance-containing gel-forming composition; and
i) disposing the fragrance-containing gel-forming composition on an interior surface of a product container or package.

Disposing the fragrance-containing gel-forming composition on an interior surface of a product container or package includes application of fragrance-containing get-forming composition as described above to an interior surface of an assembled product container or package, and also includes applying such fragrance-containing gel-forming composition to a precursor of an interior surface of a product container or package—for example to a cardboard surface which will form an interior surface after subsequent folding of the cardboard into the final package or container. Disposing the fragrance-containing gel-forming composition on an interior surface of a product container or package additionally includes application of fragrance-containing gel-forming composition onto the interior surface of a cap or lid, for example a screw-on, press-on or snap-on cap or lid. In some embodiments, the fragrance-containing gel-forming composition is disposed on an interior surface near or on a fold-out disperser, such as the paper, plastic or metal pours pouts typically used in paperboard cartoning (e.g., such as those sold by Seal-Spout Corporation).

The fragrance-containing gel-forming composition can be disposed on the interior surface of the product container or package by any convenient method, for example and not limitation by brush, spray, roller, or merely by pouring a fragrance-containing gel-forming composition onto a desired surface. For example, in one embodiment, a gelled fragrance composition is heated as described above, and the melted fragrance composition is poured into the cap or lid of the product container or package, and the fragrance composition is allowed to cool and again form a gel.

The fragrance of the fragrance-containing gel can be the same fragrance present in the product, or product container or package. Typically, the fragrance-containing gel will contain a higher concentration of fragrance than is present in the product, or product container or package. The fragrance may also be more volatile in the fragrance-containing gel than in the product contained in the product container or package. Thus, in accordance with the methods, the fragrance intensity experienced by the consumer or end-user of the product is increased.

In some embodiments, the fragrance of the fragrance-containing gel is different from the fragrance of the product, for example in the case of products whose compositions preclude incorporation of fragrance directly into the product; or where the presence of an additional fragrance, or a fragrance complementary to the fragrance in the product, is desired.

Also provided, in one embodiment, Container 1, a product container comprising a fragrance-containing gel that is disposed on the container and is not exposed to a space outside of the container, and the fragrance-containing gel is exposed to the space outside of the container upon opening of the container for dispensing a material from the container.

1.1. Container 1 wherein a product container comprises a lid, cap or cover, and the fragrance-containing gel is disposed on an interior surface of the lid, cap or cover.

1.2. Any foregoing product container wherein the product container is bottle, a jar, a carton, a box, a dispensing package; and is preferably comprised of one or more of paper, cardboard, plastic or glass.

1.3. Any foregoing product container wherein the lid, cap or cover of the product container is comprised of paper, cardboard, plastic or glass; or a combination of one or more thereof.

1.4. Any foregoing product container wherein the lid or cap is a screw cap, snap-on cap, press-on cap, a twist cap, a fold-out lid, or a fold-out or pull-out dispenser or spout (e.g., metal fold-out dispenser in dishwasher detergent boxes).

1.5. Any foregoing product container wherein the product container is:
a fabric softener or conditioner container;
a laundry detergent container (including whiteners and brighteners);
a dishwasher detergent container (for example a box, having for example a fold-out pour spout or other dispenser);
an air freshener container (including household, industrial and automobile air freshener containers and packages);
a healthcare product container or package;
a personal care product container or package, including a shower gel container, a handsoap container, a deodorant container, an antiperspirant container, a shampoo container, or conditioner container;
a candle container;
a household cleaner container, including a window cleaner container, a hard surface cleaner container, a disposable wipe container, a dish liquid container, or a dishwasher detergent container, or a rinse aid container.

1.6. Any foregoing product container wherein the product container is a fabric softener or conditioner container.

1.7. Any foregoing product container wherein the product container is a fabric softener or conditioner container having a screw cap or snap-on cap.

1.8. Any foregoing product container wherein the fragrance-containing gel contains from 30% to 95% fragrance by weight of the fragrance-containing gel; or from 45% to 95%; or from 45% to 75%; or from 75% to 95%; or from 85% to 95% fragrance by weight of the fragrance-containing gel.

1.9. Any foregoing product container wherein the fragrance-containing gel comprises the same fragrance as the product, or wherein the fragrance-containing gel comprises a different fragrance from the product.

1.10. Any foregoing product container wherein the amount of fragrance present on the interior surface of the lid, cap or cover is adjusted so as to maximize the impression of fragrance when the lid, cap or cover is opened.

1.11. Any foregoing product container wherein the fragrance containing gel contains from 85% to 95% of fragrance and is present on the interior surface of the lid, cap or cover in an amount of 0.02 to 0.2 g, e.g., 0.05 to 0.1 g, e.g. about 0.05 to 0.06 g.

1.12. Any foregoing product container wherein the container is substantially air-tight when the lid, cap or cover is in place.

1.13. Any foregoing product container wherein the lid, cap or cover is easily removeable and replaceable by a prospective consumer.

Further provided is a method of promoting the sale of a product to a consumer, comprising providing a product container comprising a fragrance-containing gel disposed on a surface thereof, wherein the fragrance can be sampled by the consumer prior to purchase. In some particular embodiments, the fragrance-containing gel is disposed on an interior surface of the product container; for example on an interior surface within the headspace of the product container, e.g., wherein the product container comprises a lid, cap or cover, wherein a fragrance-containing gel is disposed on an interior surface of the lid, cap or cover, e.g., wherein the product container is any of Container 1, et seq.

Further provided, in another embodiment, is a method for enhancing the fragrance intensity of a product in a container or a method of promoting the sale of a product to a consumer, the method comprising the step of disposing a fragrance-containing gel on an interior surface of the product container, e.g. wherein the product container is selected from any of Container 1, et seq.

In some embodiments, the methods for promoting the sale of a product to a consumer or for enhancing the fragrance intensity of a product in a container further comprise the steps of:

i) providing a fragrance-containing gel-forming composition; and ii) disposing the fragrance-containing gel-forming composition on an interior surface of a product container or package.

In another embodiment, provided is a use of a fragrance containing gel disposed on an interior surface of a lid, cap or cover of a product container for increasing fragrance perception of a product contained in the product container or for promoting the sale of a product to a consumer.

In some embodiments of the methods, the product container or package comprises a lid, cap or cover, and the fragrance-containing gel is disposed on an interior surface of the product lid, cap or cover, for example by melting a fragrance-containing gel composition, pouring the melted fragrance composition into the cap or lid, and allowing the fragrance composition to cool.

In some embodiments of the methods, the fragrance of the fragrance-containing gel is the same as the fragrance of the product, and in some further embodiments, the fragrance of the fragrance-containing gel is different from the fragrance of the product.

The following examples further illustrate the nature of the present invention, but the invention is not limited the specific examples. All amounts and proportions referred to herein and in the appended claims are by weight, unless otherwise indicated.

Example 1—Preparation of Gelled Fragrance Composition

A typical gelled fragrance suitable for use can be prepared by using an aqueous gum dispersion containing gum (Kelco-Gel gellan gum), colorant, potassium citrate (as a mold inhibitor), and a fragrance solution containing fragrance in a surfactant solution, substantially as described in U.S. Pat. No. 5,679,334. Briefly, the two dispersions are mixed and blended until the mixture is uniform in appearance, avoiding any air entrapment. While stirring the mixture and maintaining the temperature at about 60° C., the mixture becomes clear. Upon cooling to room temperature the mixture will settle as a gel. By varying the gum and fragrance those of skill in the art can achieve a desired level of loading into the gel.

Example 2—Determination of Fragrance Intensity in a Fabric Conditioner Container Containing 85% Gelled Fragrance in the Lid Fragrance intensity is determined for containers containing fabric conditioner and differing amounts of gelled fragrance (85%) disposed in the lid. Three fabric conditioner formulations containing fabric conditioner base (10% hole—i.e., fabric conditioner lacking 10% of the desired amount of water in the conditioner formulation), fragrance (Apple green variant) and water are prepared as shown in Table 1 below, and placed into containers having lids that contained either nothing (control) or 85% gelled fragrance (also Apple green variant) obtained from a commercial source.

The lids are prepared by melting the 85% gelled fragrance and pouring the melted gel composition into the lid, then allowing the composition to cool and form a gel, and finally placing the lids on the containers. After storage, the lids are removed and the fragrance intensity determined relative to the control sample by a panel of volunteers. The Results are shown in Table 2 below.

TABLE 1

|  | Fabric Conditioner Formula | | |
| --- | --- | --- | --- |
|  | A | B | C |
| Fabric Conditioner Base (10% Hole) | 90.02 | 90.01 | 90 |
| Fragrance (Apple green variant) | 0.99 | 1.02 | 1.02 |
| Water (QS) | QS | QS | QS |
| Total | 100 | 100 | 100 |

TABLE 2

|  | A | B | C |
| --- | --- | --- | --- |
| Gelled Fragrance (85%) in the lid (grams) | 0 | 0.059 | 0.118 |
| Intensity Preference versus Control | Control | Stronger | Stronger |

As can be seen from Table 2, both formulations B and C containing 85% gelled fragrance in the lid were found to be slightly stronger in intensity during neat sniffing versus Control formulation A.

Example 3—Determination of Fragrance Intensity in a Fabric Conditioner Container Containing 90% Gelled Fragrance in the Lid Fragrance intensity was determined for containers containing the same fabric conditioner base (10% Hole) as in Example 2, microcapsules containing 35% fragrance, and a traditional fragrance used in fabric conditioners (Fragrance 1), with 90% gelled fragrance in the lid. The compositions of the formulations are shown in Table 3 below, and the results of the Intensity Evaluation Test are shown in Table 4 below.

TABLE 3

|  | Fabric Conditioner Formula | | | | |
| --- | --- | --- | --- | --- | --- |
|  | D | E | F | G | H |
| Fabric Conditioner Base (10% Hole) | 90 | 90 | 90 | 90 | 90 |
| Fragrance 1 | 0.5 | 0.4 | 0.45 | 0.5 | 0.5 |
| Microcapsules (35% Fragrance) | 1.61 | 1.61 | 1.61 | 1.61 | 1.61 |
| Water (QS) | QS | QS | QS | QS | QS |
| Total | 100 | 100 | 100 | 100 | 100 |

TABLE 4

|  | D | E | F | G | H |
| --- | --- | --- | --- | --- | --- |
| Gelled Fragrance (90%) in the lid (grams) | 0 | 0.11 | 0.055 | 0.05 | 0.11 |
| Intensity Preference versus Control | Control | Parity | Better | Better | Parity |

Example 4—Determination of Fragrance Intensity in a Fabric Conditioner Container Containing 95% Gelled Fragrance in the Lid Fragrance intensity was determined for containers containing the same fabric conditioner base (10% Hole) as in Examples 2 and 3, microcapsules containing 35% fragrance, and a different traditional fragrance used in fabric conditioners (Fragrance 2), with 95% gelled fragrance in the lid. The compositions of the formulations are shown in Table 5 below, and the Results of the Intensity Evaluation Test are shown in Table 6 below.

TABLE 5

|  | Fabric Conditioner Formula | | | | |
| --- | --- | --- | --- | --- | --- |
|  | I | J | K | L | M |
| Fabric Conditioner Base (10% Hole) | 90 | 90 | 90 | 90 | 90 |
| Fragrance 2 | 0.5 | 0.4 | 0.45 | 0.5 | 0.5 |
| Microcapsules (35% Fragrance) | 1.61 | 1.61 | 1.61 | 1.61 | 1.61 |
| Water (QS) | QS | QS | QS | QS | QS |
| Total | 100 | 100 | 100 | 100 | 100 |

TABLE 6

|  | I | J | K | L | M |
| --- | --- | --- | --- | --- | --- |
| Gelled Fragrance (95%) in the lid (grams) | 0 | 0.105 | 0.053 | 0.053 | 0.105 |
| Intensity Preference versus Control | Control | Parity | Better | Better | Parity |

The data indicate that 0.050-0.055 grams of gelled fragrance deposited in the lid of the tested containers produced a more intense fragrance in the tested containers than lesser or greater amounts.

The formulations from Tables 3 and 5 containing fragrance and gelled fragrance, and their corresponding controls were evaluated by a panel of volunteers to simulate the point of purchase effect that would be experienced by a consumer. After sufficient maturation, the containers were evaluated tier odor intensity by opening each container and sniffing the odor directly, and rating the odor for intensity, as indicated in Tables 4 and 6.

Among the formulations from Table 3, formulas F and G were found to be better than Control formula D. Similarly, among the formulations from Table 5, formulas K and L were fount to be better than Control formula I.

Studies were repeated using formulations containing other fragrances and found to have similar results in improving the perceived fragrance intensity.

Taken together, the data above indicate that the intensity of fragrance in the head space of the container from the formulation was increased by addition of gelled fragrance in the lid of the container, and this enhancement is perceivable by consumers.

What is claimed is:

1. A product container comprising:
    a lid, cap or cover,
    a product comprising a first fragrance; and
    a fragrance-containing gel comprising a second fragrance,
    wherein the fragrance-containing gel is disposed on an interior surface of the lid, cap or cover and is not exposed to a space outside of the product container until the lid, cap or cover is at least partially removed;
    wherein the concentration of the second fragrance in the fragrance-containing gel is greater than the concentration of the first fragrance in the product; and
    wherein the fragrance-containing gel contains 85 to 95 weight % of the second fragrance and is present on the interior surface of the lid, cap or cover in an amount of 0.02 to 0.2 g.

2. The product container of claim 1, wherein the product container further comprises headspace; wherein the interior surface of the lid, cap or cover is within the head space.

3. The product container of claim 1, wherein the product container comprises one or more of paper, cardboard, plastic or glass; and is in the form of a bottle, a jar, a carton, a box, or a dispensing package.

4. The product container of claim 1, wherein the product container is selected from the group consisting of: a fabric softener or conditioner container; a laundry detergent container; a dishwasher detergent container; an air freshener container; a healthcare product container or package; a personal care product container or package; a shower gel container; a handsoap container; a deodorant container; an antiperspirant container; a shampoo container; conditioner container; a candle container; a household cleaner container; a window cleaner container; a hard surface cleaner container; a disposable wipe container; a dish liquid container; and a rinse aid container.

5. The product container of claim 1, wherein the product container is a fabric softener or conditioner container.

6. The product container of claim 1, wherein the container is air-tight when the lid, cap or cover is in place.

7. The product container of claim 1, wherein the lid, cap or cover is removeable and replaceable by a prospective consumer.

8. A method for enhancing the fragrance intensity of a fragrance-containing product in a container, the method comprising the step of
    disposing a fragrance-containing gel on an interior surface of a lid, cap or cover of the container,
    wherein the fragrance-containing gel contains 85 to 95 weight % of a fragrance and is present on said interior surface in an amount of 0.02 to 0.2 g, and
    wherein the concentration of the fragrance in the fragrance-containing gel is greater than the concentration of the fragrance in the fragrance-containing product.

9. The method of claim 8, wherein the fragrance-containing gel-forming composition is provided at an elevated temperature and disposed on the interior surface of the product container or package at the elevated temperature; and then allowed to cool and form the fragrance-containing gel.

10. The method of claim 8, wherein the product container comprises one or more of paper, cardboard, plastic or glass; and is in the form of a bottle, a jar, a carton, a box, or a dispensing package.

11. A method of promoting a fragrance-containing product to a consumer, comprising providing a product container comprising a fragrance-containing gel disposed on an interior surface of a lid, cap or cover thereof,
    wherein the fragrance-containing gel contains 85 to 95 weight % of a fragrance and is present on said interior surface in an amount of 0.02 to 0.2 g,
    wherein the fragrance can be sampled by the consumer by opening the product container to access the fragrance-containing gel disposed on the interior surface; and
    wherein the concentration of the fragrance in the fragrance-containing gel is greater than the concentration of the fragrance in the fragrance-containing product.

12. The method of claim 11, further comprising the steps of:
   i) providing a fragrance-containing gel-forming composition; and
   ii) disposing the fragrance-containing gel-forming composition on an interior surface of a product container or package.

13. The method of claim 11, wherein the fragrance-containing gel-forming composition is provided at an elevated temperature and disposed on the interior surface of the product container or package at the elevated temperature; and then allowed to cool and form the fragrance-containing gel.

14. The method of claim 11 wherein the product container comprises one or more of paper, cardboard, plastic or glass; and is in the form of a bottle, a jar, a carton, a box, or a dispensing package.

15. The method of claim 11, wherein when the product container is opened, the fragrance-containing gel increases the apparent fragrance intensity of a product contained in the product container to the consumer.

16. The method of claim 15, wherein the product container comprises one or more of paper, cardboard, plastic or glass; and is in the form of a bottle, a jar, a carton, a box, or a dispensing package.

* * * * *